United States Patent [19]

Biller et al.

[11] Patent Number: 5,254,544
[45] Date of Patent: Oct. 19, 1993

[54] HYDROXYPHOSPHINYL PHOSPHONATE SQUALENE SYNTHETASE INHIBITORS AND METHOD

[75] Inventors: Scott A. Biller, Ewing; John K. Dickson, Jr., Mount Holly, both of N.J.

[73] Assignee: E. R. Squibb & Sons, Inc., Princeton, N.J.

[21] Appl. No.: 950,555

[22] Filed: Sep. 25, 1992

[51] Int. Cl.⁵ ............................ A61K 31/66; C07F 9/48
[52] U.S. Cl. ..................................... 514/107; 514/39; 514/54; 514/108; 558/155; 558/161; 562/21
[58] Field of Search .................. 558/155, 161; 562/21; 514/107, 108

[56] References Cited

U.S. PATENT DOCUMENTS 4,871,721 10/1989 Biller .................... 514/102

FOREIGN PATENT DOCUMENTS 0298553 1/1989 European Pat. Off. .
0356866A of 1990 European Pat. Off. .
0409181A2 1/1991 European Pat. Off. .
50-095227 7/1975 Japan .

OTHER PUBLICATIONS

Prischenko et al, *Zh. Obsch. Khim*, 1977, 47, 2689–2698.

Primary Examiner—Mary C. Lee
Assistant Examiner—Michael G. Ambrose
Attorney, Agent, or Firm—Burton Rodney

[57] ABSTRACT

Hydroxyphosphinyl phosphonate compounds are provided which inhibit the enzyme squalene synthetase and thereby inhibit cholesterol biosynthesis. These compounds have the formula

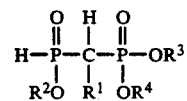

wherein $R^2$, $R^3$ and $R^4$ are independently H, alkyl, metal ion or a prodrug ester; and $R^1$ is a lipophilic group which contains at least 6 carbons and is alkyl, alkenyl, alkynyl, mixed alkenylalkynyl, a hetero-containing moiety as defined herein, or a phenylalkyl or phenylalkenyl group including those containing a biphenyl group.

18 Claims, No Drawings

HYDROXYPHOSPHINYL PHOSPHONATE SQUALENE SYNTHETASE INHIBITORS AND METHOD

FIELD OF THE INVENTION

The present invention relates to new hydroxyphosphinyl phosphonate compounds which are useful in inhibiting cholesterol biosynthesis by inhibiting de novo squalene production, to hypocholesterolemic and antiatherosclerotic compositions containing such compounds and to a method of using such compounds for inhibiting cholesterol biosynthesis and atherosclerosis.

BACKGROUND OF THE INVENTION

Squalene synthetase is a microsomal enzyme which catalyzes the reductive dimerization of two molecules of farnesyl pyrophosphate (FPP) in the presence of nicotinamide adenine dinucleotide phosphate (reduced form) (NADPH) to form squalene (Poulter, C. D.; Rilling, H. C., in "Biosynthesis of Isoprenoid Compounds", Vol. I, Chapter 8, pp. 413–441, J. Wiley and Sons, 1981, and references therein). This enzyme is the first committed step of the de novo cholesterol biosynthetic pathway. The selective inhibition of this step should allow the essential pathways to isopentenyl tRNA, ubiquinone, and dolichol to proceed unimpeded. Squalene synthetase along with HMG-CoA reductase have been shown to be down-regulated by receptor mediated LDL uptake (Faust, J. R.; Goldstein, J. L.; Brown, M. S. *Proc. Nat. Acad. Sci. U.S.A.* 1979, 76, 5018–5022), lending credence to the proposal that inhibiting squalene synthetase will lead to an up-regulation of LDL receptor levels, as has been demonstrated for HMG-CoA reductase, and thus ultimately should be useful for the treatment and prevention of hypercholesterolemia and atherosclerosis.

European Patent Publication 0409181A3 discloses phosphorus-containing compounds which are inhibitors of cholesterol biosynthesis (by inhibiting de novo squalene biosynthesis), and thus are useful as hypocholesterolemic agents and antiatherosclerotic agents, which have the structure

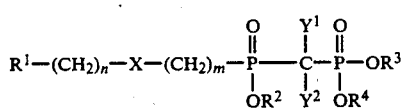

wherein
m is 1, 2 or 3; n is 0, 1, 2, or 3;
$Y^1$ and $Y^2$ are H or halogen;
$R^2$, $R^3$ and $R^4$ may be the same or different and are independently H, metal ion, $C_1$ to $C_8$ alkyl or $C_3$ to $C_{12}$ alkenyl;
X is O, S, NH or $NCH_2R^{15}$ wherein $R^{15}$ is H or $C_1$ to $C_5$ alkyl; and
$R^1$ is $R^5—Q^1—Q^2—Q^3—$ wherein $Q^1$, $Q^2$ and $Q^3$ are the same or different and are independently

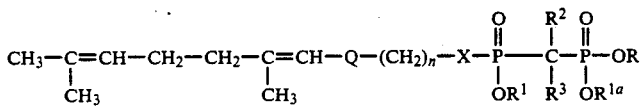

a single bond, with the proviso that if $Q^1$ is a bond, then $Q^2$ and $Q^3$ are bonds and if $Q^2$ is a bond, then $Q^3$ is a bond, and wherein $R^6$ is H, alkyl, halo, or haloalkyl; $R^7$ is H, halo, alkyl or alkylthio; $R^8$ is H, halogen, trimethylsilyl or lower alkyl; $R^9$ is H or lower alkyl-;

$R^5$ is

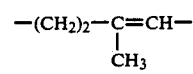

$R^{16}—C≡C—CH_2—$ (wherein $R^{16}$ is H or lower alkyl) or $CH_3(CH_2)_p$ where p is an integer from 2 to 7; $R^{10}$, and $R^{11}$ are the same or different and are independently H, lower alkyl, halogen, haloalkyl or lower alkenyl or $R^{10}$ and $R^{11}$ can be taken together to form $(CH_2)_s$ where s is an integer from 2 to 7; and $R^{13}$ and $R^{14}$ are the same or different and are independently lower alkyl, with the proviso that if all of $Q^1$, $Q^2$ and $Q^3$ are bonds, then both $R^{10}$ and $R^{11}$ cannot be H and $R^5$ cannot be alkyl($CH_2$-$)_p$— with $p≦4$; including all stereoisomers thereof.

European Patent Publication 0356866A2 discloses phosphorus-containing compounds which inhibit the enzyme squalene synthetase and thus are useful as hypocholesterolemic agents and have the following structure $$CH_3-\underset{\underset{CH_3}{|}}{C}=CH-CH_2-CH_2-\underset{\underset{CH_3}{|}}{C}=CH-Q-(CH_2)_n-X-\underset{\underset{OR^1}{|}}{\overset{\overset{O}{\|}}{P}}-\underset{\underset{R^3}{|}}{\overset{\overset{R^2}{|}}{C}}-\underset{\underset{OR^{1a}}{|}}{\overset{\overset{O}{\|}}{P}}-OR$$

wherein
Q is $$-(CH_2)_2-\underset{\underset{CH_3}{|}}{C}=CH-$$

or a bond;
n is 1, 2, 3 or 4;
X is —O—, —NH—, or —$NR^4$—;
R, $R^1$ and $R^{1a}$ may be the same or different and are H, lower alkyl, lower alkenyl or a metal ion;
$R^2$ and $R^3$ may be the same or different and are H or halogen;
$R^4$ is lower alkyl;
with the proviso that when X is 0, n is 2, 3 or 4.

U.S. Pat. No. 4,871,721 to Biller et al. discloses phosphorus-containing compounds which inhibit the enzyme squalene synthetase and thus are useful as hypocholesterolemic agents and have the following structure

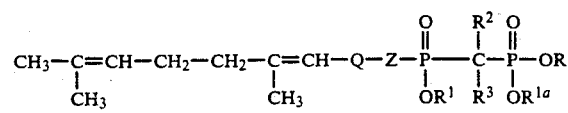

wherein
Q is

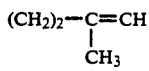

or a bond;

Z is —(CH$_2$)$_n$— or —(CH$_2$)$_p$—CH=CH—(CH$_2$)$_m$—, wherein n is 1 to 5; p is 0, 1 or 2; m is 0, 1 or 2;

R, R$^1$ and R$^{1a}$ may be the same or different and are H, lower alkyl or a metal ion; and R$^2$ and R$^3$ may be the same or different and are H or halogen.

European Patent Application 0298553 A1 discloses bone active methylene phosphonoalkylphosphinic acids, and the pharmaceutically-acceptable salts and esters thereof, having the general structure:

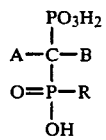

R can be H or substituted or unsubstituted alkyl, each of A and B can be H as well as substituted or unsubstituted alkyl as well as other groups as disclosed. However, EP 0298553 A1 does not disclose how to prepare compounds where R is H.

Japanese Patent 50095227 (1975) to Sakurai et al. discloses compounds of the structure

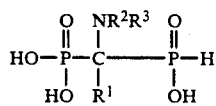

wherein R$^1$ is H or alkyl, and R$^2$ and R$^3$ are alkyl or aryl, which are prepared by reacting amide

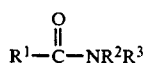

with phosphorus trichloride.

Prishchenko et al., and Novikova, et al., Zh. Obsch. Khim., 1977, 47, 2689-2698 disclose the following reactions:

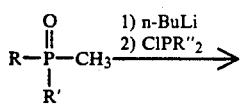

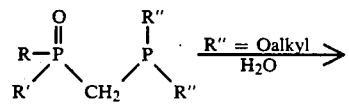

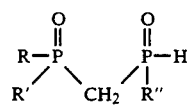

R, R', R''=alkyl, Oalkyl, Nalkyl$_2$

DESCRIPTION OF THE INVENTION

In accordance with the present invention, there is provided hydroxyphosphinyl phosphonate compounds which inhibit cholesterol biosynthesis, and thus are useful as hypocholesterolemic and antiatherosclerotic agents and have the following structure

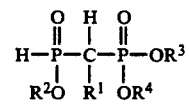

wherein R$^2$, R$^3$ and R$^4$ are independently H, alkyl, aryl or metal ion;

R$^1$ is a lipophilic group containing at least 6 carbons, and preferably from about 7 to about 35 carbons, and is preferably alkyl containing from 7 to about 25 carbons, alkenyl containing from 7 to 25 carbon atoms in the chain and from 1 to 4 double bonds; alkynyl containing 1 to 4 triple bonds; mixed alkenyl-alkynyl containing to 3 double bonds and 1 to 3 triple bonds, and where in the above groups alkyl, alkenyl and/or alkynyl may be substituted or unsubstituted; or a group of the structure

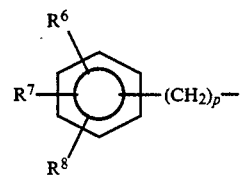

wherein (CH$_2$)$_p$ contains from 1 to 15 carbons, preferably 2 to 12 carbons, in the chain and may include 0, 1, 2 or 3 double bonds and/or 0, 1, 2 or 3 triple bonds in the normal chain, and/or may include 0, 1, 2 or 3 substituents; and R$^6$, R$^7$ and R$^8$ are the same or different and are H, alkyl containing 1 to 40 carbons, preferably from 3 to 15 carbons, alkoxy containing 1 to 40 carbons, preferably from 3 to 15 carbons, alkenyl containing 2 to 40 carbons, preferably from 3 to 15 carbons, alkenyloxy containing 2 to 40 carbons, preferably from 3 to 15 carbons, alkynyl containing 2 to 40 carbons, preferably from 3 to 15 carbons, alkynyloxy containing 2 to 40 carbons, preferably from 3 to 15 carbons, aryl, aryloxy, hydroxy, halogen, nitro, amino, thiol, alkylthio, aryl, arylthio, alkyl-sulfinyl, arylsulfinyl, alkylsulfonyl, arylsul-fonyl, carboxy, alkoxycarbonyl, aminocarbonyl, alkylcarbonyloxy, arylcarbonyloxy, arylcarbonylamino or alkyl carbonylamino, preferably at least one of R$^6$, R$^7$ and R$^8$ being alkyl, alkoxy, aryl aryloxy, alkenyl, alkenyloxy, alkynyl or alkynyloxy; and preferably wherein the total number of carbons in the substituted phenyl(CH$_2$)$_p$— group exceeds 10 carbons; and including pharmaceutically acceptable salts.

The (CH$_2$)$_p$ group may contain one or more alkyl, alkoxy, alkenyl, alkynyl, hydroxy and/or halogen substituents.

Unless otherwise indicated, the term "lower alkyl" or "alkyl" as employed herein alone or as part of another group includes both straight and branched chain hydrocarbons, containing 1 to 40 carbons, preferably 1 to 20 carbons, in the normal chain, more preferably 1 to 12 carbons, such as methyl, ethyl, propyl, isopropyl, butyl, t-butyl, isobutyl, pentyl, hexyl, isohexyl, heptyl, 4,4- dimethylpentyl, octyl, 2,2,4-trimethylpentyl, nonyl, decyl, undecyl, dodecyl, the various branched chain isomers thereof, and the like as well as such groups including 1 to 4 substituents such as F, Br, Cl or I or CF$_3$, alkoxy, aryl, arylalkyl, alkenyl, cycloalkyl, amino, hydroxy, alkylamido, alkanoylamino, arylcarbonylamino, nitro, cyano, thiol and/or alkylthio.

Unless otherwise indicated, the term "cycloalkyl" as employed herein alone or as part of another group includes saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl, any of which groups may be substituted with 1 to 4 substituents such as halogen, alkyl, alkoxy, hydroxy, aryl, arylalkyl, cycloalkyl, alkylamido, alkanoylamino, arylcarbonylamino, amino, nitro, cyano, thiol and/or alkylthio.

Unless otherwise indicated, the term "aryl" or "Ar" as employed herein refers to monocyclic or bicyclic aromatic groups containing from 6 to 10 carbons in the ring portion, such as phenyl, naphthyl or phenyl or naphthyl substituted with 1 to 3 substituents such as alkyl, halogen (Cl, Br or F), alkoxy, hydroxy, amino, alkanoylamino, arylcarbonylamino, aryl, arylalkyl, cycloalkyl, alkylamido, nitro, cyano, thiol and/or alkylthio.

The term "aralkyl", "aryl-alkyl" or "aryl-lower alkyl" as used herein alone or as part of another group refers to alkyl groups as discussed above having an aryl substituent, such as benzyl or phenethyl.

The term "lower alkoxy", "alkoxy", "aryloxy" or "aralkoxy" as employed herein alone or as part of another group includes any of the above alkyl, aralkyl or aryl groups linked to an oxygen atom.

The term "lower alkylthio", "alkylthio", "arylthio" or "aralkylthio" as employed herein alone or as part of another group includes any of the above alkyl, alkyl, aralkyl or aryl groups linked to a sulfur atom.

The term "lower alkylamino", "alkylamino", "arylamino", or "arylalkylamino" as employed herein alone or as part of another group includes any of the above alkyl, aryl or arylalkyl groups linked to a nitrogen atom.

The term "alkanoyl" as used herein alone or as part of another group refers to alkyl linked to a carbonyl group.

Unless otherwise indicated, the term "lower alkenyl" or "alkenyl" as used herein by itself or as part of another group refers to straight or branched chain radicals of 2 to 40 carbons, preferably 3 to 30 carbons in the normal chain, which include one to three double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl and the like, and which may be optionally substituted with 1 to 4 substituents, namely, halogen, alkyl, alkoxy, alkenyl, alkynyl, aryl, alkenyloxy, alkynyloxy, arylalkyl, cycloalkyl, amino, hydroxy, alkanoylamino, alkylamido, arylcarbonylamino, nitro, cyano, thiol and/or alkylthio.

Unless otherwise indicated, the term "lower alkynyl" or "alkynyl" as used herein by itself or as part of another group refers to straight or branched chain radicals of 2 to 40 carbons, preferably 2 to 20 carbons in the normal chain, which include one triple bond in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl and the like, and which may be optionally substituted with 1 to 4 substituents, namely, halogen, alkyl, alkoxy, alkenyl, alkynyl, aryl, arylalkyl, alkenyloxy, alkynyloxy, cycloalkyl, amino, hydroxy, alkanoylamino, alkyl-amido, arylcarbonylamino, nitro, cyano, thiol, and/or alkylthio.

Examples of suitable (CH$_2$)$_p$ groups include

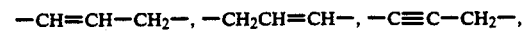

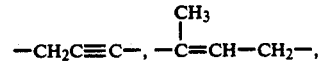

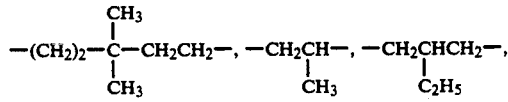

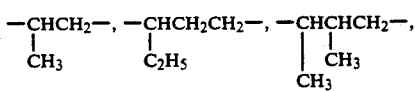

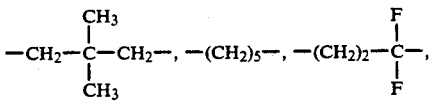

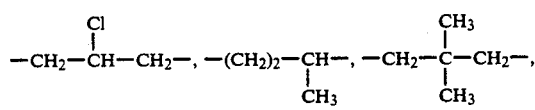

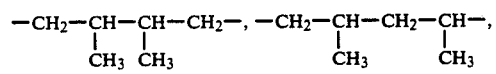

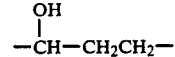

The term "halogen" or "halo" as used herein refers to chlorine, bromine, fluorine, and iodine as well as CF$_3$, with chlorine or fluorine being preferred.

The term "amino" as used herein refers to unsubstituted amino as well as monosubstituted amino or disubstituted amino wherein the substituents may be alkyl and/or aryl.

The term "metal ion" refers to alkali metal ions such as sodium, potassium or lithium and alkaline earth metal ions such as magnesium and calcium.

Preferred are compounds of formula I, wherein R$^2$, R$^3$ and R$^4$ are each a metal ion such as Na or K. H, alkyl such as CH$_3$ or C$_2$H$_5$; and R$^1$ is alkenyl or biphenylalkyl.

The compounds of the invention may be prepared according to the following reaction sequences.

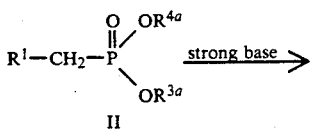

-continued

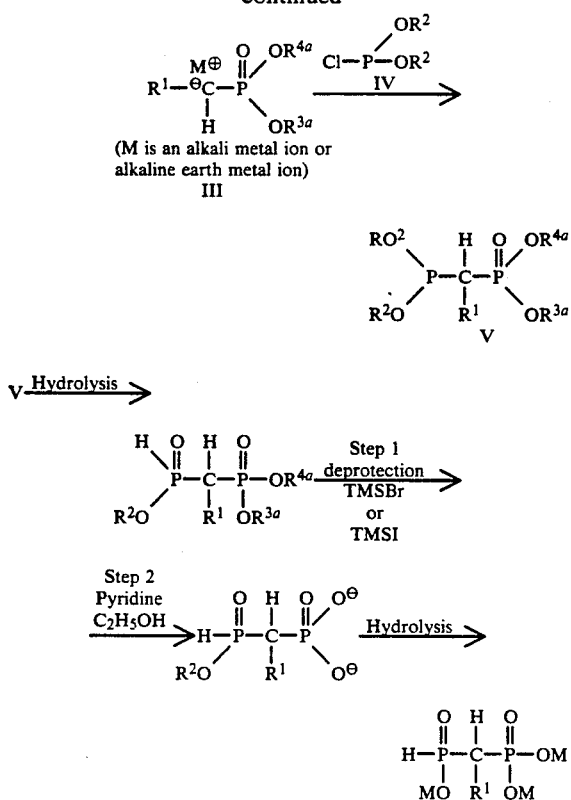

(M is an alkali metal ion or alkaline earth metal ion)
III

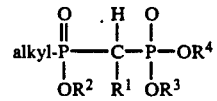

As seen in the above reaction scheme, compounds of formula I of the invention may be prepared starting with a solution phosphonate II in an inert organic solvent such as tetrahydrofuran or diethyl ether, or mixtures of the above with pentane, hexane or cyclohexane, which is treated with a strong base such as n-butyllithium, t-butyllithium, or lithium diisopropyl amide, at a temperature of within the range of from about −100° C. to about 0° C., and preferably from about −80° C. to about −20° C., to form the anion III. The above reaction is carried out employing a molar ratio of strong base to phosphonate II of within the range of from about 0.8:1 to about 4:1, and preferably from about 1: to about 1.2:1.

The reaction mixture containing anion III is then treated with dialkylchlorophosphite IV employing a molar ratio of IV:III of within the range of from about 1:1 to about 20:1, and preferably from about 1:1 to about 5:1, and a temperature of within the range of from about −100° to about 30° C. and preferably from about −80° to about 25° C., to form intermediate V which is hydrolyzed by quenching the reaction mixture with water to form the phosphonous ester IA of the invention.

Phosphonous ester IA is then deprotected by treating IA with bromotrimethylsilane (TMSBr) or iodotrimethylsilane (TMSI) together with bis(trimethylsilyl)trifluoroacetamide or allyltrimethylsilane in dichloromethane under an inert atmosphere such as argon, and then treated with a solution of pyridine in ethanol to form ester IB. The salt IC is then obtained by subjecting IB to hydrolysis in the presence of alkali metal base or an alkaline earth metal base (MOH).

The phosphonous ester IA of the invention may be used to prepare squalene synthetase inhibitors, for example, by alkylating IA by deprotonation with one equivalent of base followed by treatment with an alkylating agent (such as an alkyl halide) or via exposure to trimethylsilyl chloride and triethylamine in the presence of an alkylating agent. Alkylation occurs selectively on the phosphorus atom instead of on the carbon alpha to the 2 phosphorus atoms. The resulting protected intermediate of the structure VI

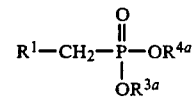

in an inert organic solvent such as methylene chloride, may then be subjected to deprotection by treating VI with excess bromotrimethylsilane or iodotrimethylsilane in the presence of 2,4,6-collidine, bis(trimethylsilyl)trifluoroacetamide, allyltrimethylsilane or hexamethyldisilazane, and then treating with a strong inorganic base such as aqueous NaOH, KOH, LiOH or Mg(OH)$_2$, optionally in the presence of an alcohol such as methyl alcohol, to form the corresponding salt which may be separated out by chromatography. The so-formed salt may be treated with a strong acid such as HCl to form the corresponding acid.

The phosphonate II starting material

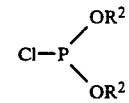

wherein $R^{3a}$ and $R^{4a}$ are alkyl and $R^1$ is a lipophilic group containing at least 6 carbons may be prepared by many known methods, including those found in:

Kosolapoff, G. M.; Maier, L., eds. *Organic Phosphorus Compounds*, Wiley, Vol. 7, 1976.

Engel, R., *Synthesis of Carbon-Phosphorus Bonds*, CRC Press, 1988.

The dialkyl chlorophosphite IV starting material $$Cl-P\begin{matrix}OR^2\\OR^2\end{matrix} \qquad IV$$

may be prepared by many known methods, including those found in Kosolapoff, G. M.; Maier, L., eds. *Organic Phosphorus Compounds*, Wiley, Vol. 5, 1973.

Examples of starting material II suitable for use herein include the following which are either known in the literature or are simple derivatives of known compounds prepared by employing conventional procedures as described above or in the literature.

It will be appreciated that the compounds listed in the following table represent all possible stereoisomers.

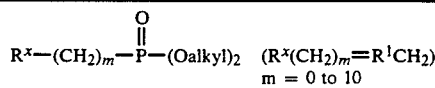

-continued

| $R^x$ | | |
|---|---|---|

A.

R¹⁷\C=CH-CH₂-CH₂-C(CH₃)=CH-CH₂-CH₂-C(CH₃)=CH-CH₂— or
R¹⁸/

R¹⁷\C=CH-CH₂-CH₂-C(CH₃)=CH-CH₂—
R¹⁸/

| | $R^{17}$ | $R^{18}$ |
|---|---|---|
| 1. | $C_2H_5$ | $CH_3$ |
| 2. | $CH_3$ | $C_2H_5$ |
| 3. | $n\text{-}C_3H_7$ | $CH_3$ |
| 4. | $CH_3$ | $n\text{-}C_4H_9$ |
| 5. | $t\text{-}C_4H_9$ | $CH_3$ |
| 6. | $-(CH_2)_{s'}-$ $s' = 4$ to $6$ | |
| 7. | H | H |
| 8. | F | F |
| 9. | Cl | Cl |
| 10. | $CH_2F$ | $CH_3$ |
| 11. | $-CH=CH_2$ | H |

B.

alkyl-(CH₂)ₜ-C(CH₃)=CH-CH₂-C(CH₃)=CH-CH₂— or alkyl-(CH₂)ₜ-C(CH₃)=CH-CH₂—

1. alkyl(CH₂)ₜ—
   $CH_3(CH_2)_t$ where t is 0 to 7

2. $(CH_3)_2CH-(CH_2)_t-$ where t is 0 to 7

3. cyclohexyl-(CH₂)ₜ— where t is 0 to 7

4. phenyl-(CH₂)ₜ— where t is 0 to 7

C.

$CH_3-C(CH_3)=C-CH_2+(CH_2-C(CH_3)=C-CH_2)_t$
t = 0, 1, 2, 3

$H-C(CH_3)_2-CH_2-CH_2+(CH_2-CH(CH_3)-CH_2-CH_2)_t$
t = 0, 1, 2, 3

D.

$CH_3\text{-}C(R^{21})=CH\text{-}CH_2\text{-}C(R^{22})=CH\text{-}CH_2\text{-}C(R^{23})=CH\text{-}CH_2-$ or $CH_3\text{-}C(R^{21})=CH\text{-}CH_2\text{-}C(R^{22})=CH\text{-}CH_2-$ -continued
|   | $R^{21}$ | $R^{22}$ | $R^{22}$ |
|---|---|---|---|
| 1. | $C_2H_5$ | $C_2H_5$ | $CH_3$ |
| 2. | $CH_3$ | $CH_3$ | $C_2H_5$ |
| 3. | $CH_3$ | $C_2H_5$ | $C_2H_5$ |
| 4. | $C_2H_5$ | $C_2H_5$ | $C_2H_5$ |
| 5. | $CH_3$ | $C_2H_5$ | $CH_3$ |
| 6. | $CH_3$ | H | $CH_3$ |
| 7. | $CH_3$ | $CH_3$ | H |
| 8. | H | H | H |
E.
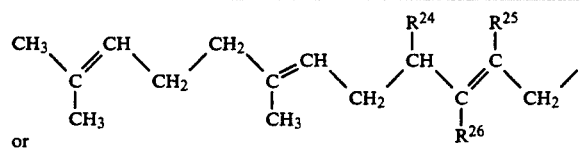
or
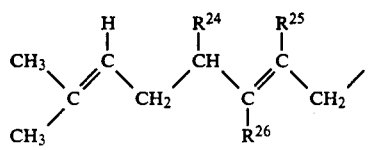
|   | $R^{24}$ | $R^{25}$ | $R^{26}$ |
|---|---|---|---|
| 1. | H | I | H |
| 2. | H | H | I |
| 3. | H | $CH_3$ | $CH_3$ |
| 4. | $CH_3S$ | $CH_3$ | H |
| 5. | F | $CH_3$ | H |
| 6. | $CH_3$ | $CH_3$ | H |
| 7. | H | $CH_3$ | $CH_3$ |
| 8. | H | $CH_3$ | Cl |
| 9. | H | $CF_3$ | H |
| 10. | H | Cl | H |
| 11. | H | $CH_3$ | $(CH_3)_3Si$ |
| 12. | H | $CH_3$ | F |
F. Other examples of $R^x$ include the following
1. 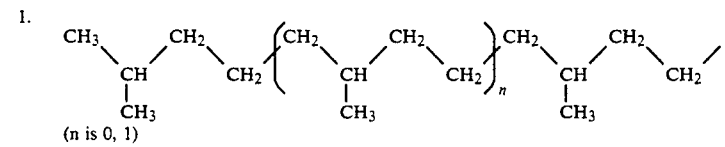
(n is 0, 1)
2. 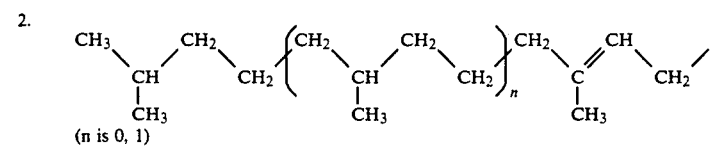
(n is 0, 1)
3. 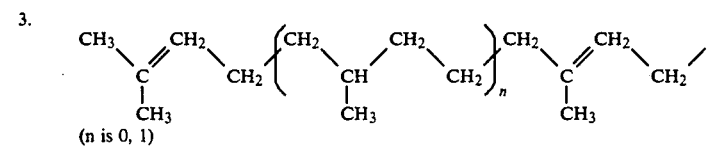
(n is 0, 1)
4. 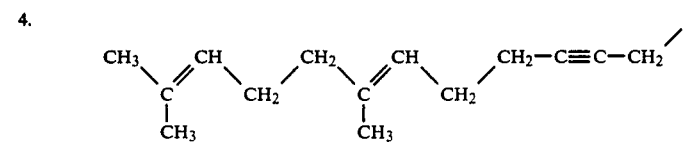
5. 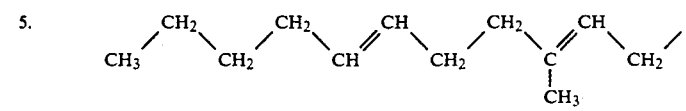

-continued
6. 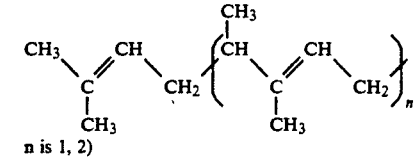
(n is 1, 2)
7. 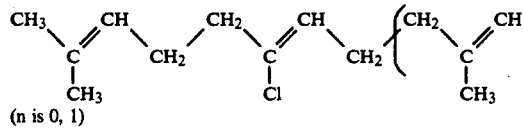
(n is 0, 1)
8. 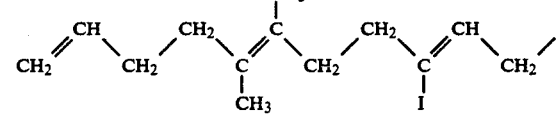
9. 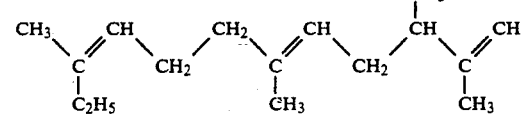
10. 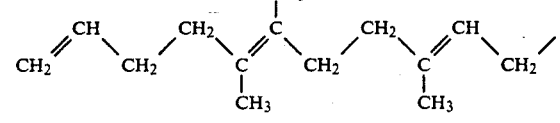
11. 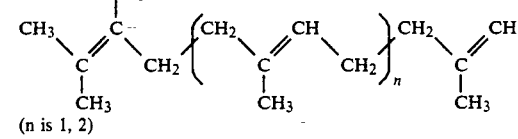
(n is 1, 2)
12. 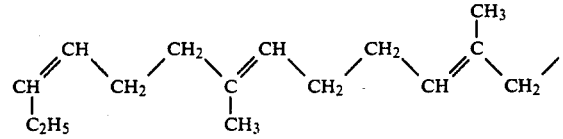
13. 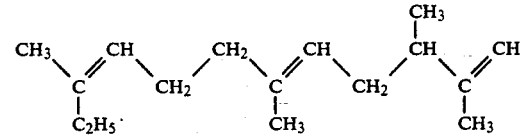
14. 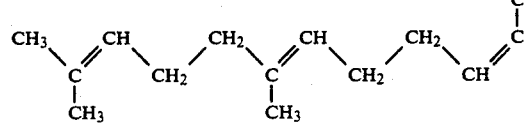
15. 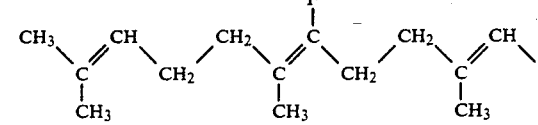

-continued
16. 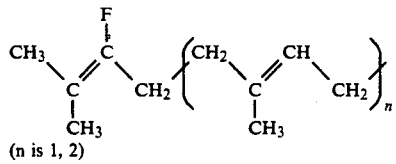
(n is 1, 2)
17. 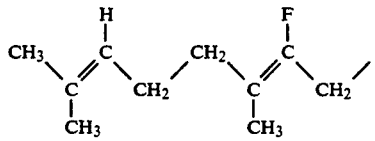
18. 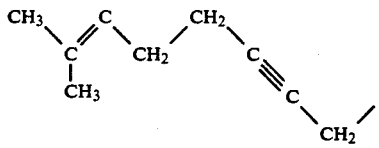
19. 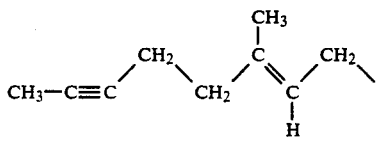
20. $CH_3-C\equiv C-(CH_2)_n-$ (n = 4-12)
21. $CH_3-C\equiv C-(CH_2)_n-C\equiv C-CH_2-$ (n = 2-10)
22. 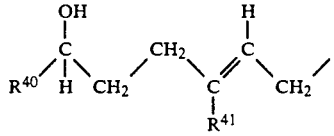
$R^{40}$=H, alkyl, cycloalkyl, or aryl such as methyl, ethyl, isopropyl, pentyl, phenyl and cyclopentyl
$R^{41}$=alkyl such as methyl, ethyl or halo such as Cl or F
23. 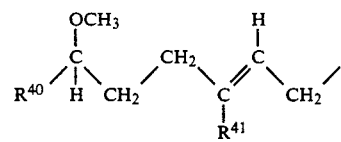
24. 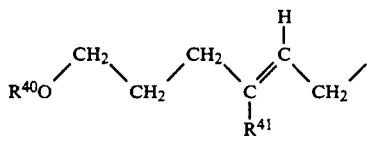
25. 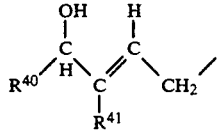
26. 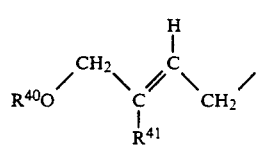
-continued
27. 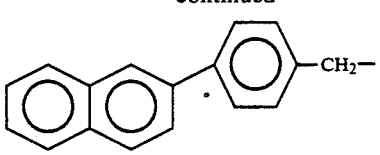
28. 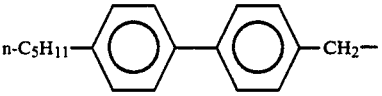
29. 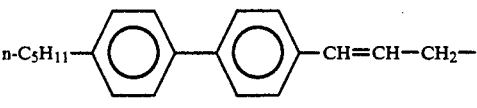
30. 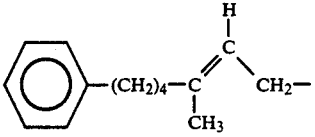
31. 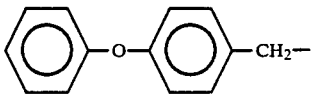
32. 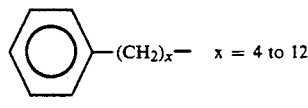 x = 4 to 12

-continued

33. 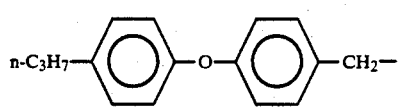

33a. $C_tH_{2t+1}$, t = 6-20

34. 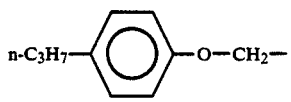

35. 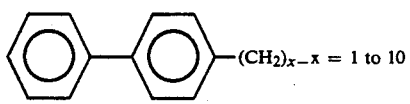 $(CH_2)_x$— x = 1 to 10

36. 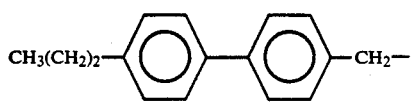

37. 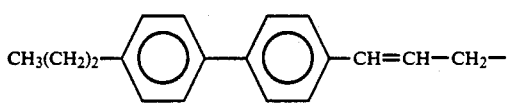

38. 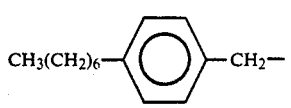

39. 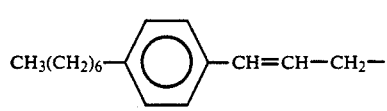

40. 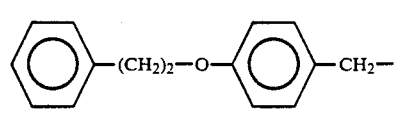

41. 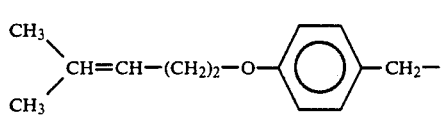

42. 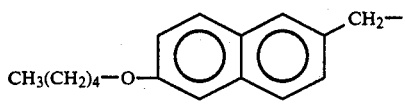

Additional compounds within the scope of the present invention are set out below.

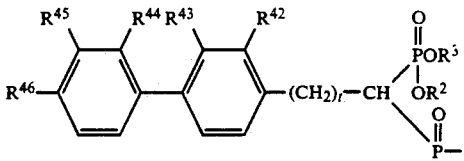

| | $R^{42}$ | $R^{43}$ | $R^{44}$ | $R^{45}$ | $R^{46}$ | t |
|---|---|---|---|---|---|---|
| 45) | H | H | H | H | $CH_3$ | 3 |
| 46) | H | H | H | H | $CF_3$ | 3 |
| 47) | H | H | H | H | $NO_2$ | 4 |
| 48) | H | H | H | H | $NH_2$ | 2 |
| 49) | $CH_3$ | H | H | H | $CH_3$ | 3 |
| 50) | H | H | $CH_3$ | H | H | 3 |
| 51) | H | $CH_3$ | $CH_3$ | H | $(CH_2)_3CH_3$ | 3 |
| 52) | $CH_3O$ | H | H | H | H | 3 |
| 53) | H | H | H | H | $CH_3O$ | 3 |
| 54) | H | H | H | H | Cl | 4 |
| 55) | $CH_3$ | H | H | H | $\underset{\underset{\parallel}{O}}{NHCCH_3}$ | 5 |
| 56) | F | H | $CH_3$ | H | $(CH_2)_4CH_3$ | 3 |
| 57) | $CH_3$ | H | H | H | OH | 3 |
| 58) | H | H | H | $CH_3$ | H | 3 |
| 59) | H | H | H | $CF_3$ | H | 3 |
| 60) | H | H | H | F | H | 3 |
| 61) | H | Cl | Cl | H | H | 3 |
| 62) | $CH_3$ | H | H | H | $C_4H_9$ | 3 |

$R^2$ = H, metal ion or alkyl
$R^3$ = H, metal ion or alkyl
$R^4$ = H, metal ion or alkyl 63. [structure with 2,6-dimethylbiphenyl]

64. [structure with 2,6-dimethylbiphenyl variant]

$x^1$ = —$(CH_2)_n$—, —CH=CH—$CH_2$—
n = 2, 5

The compounds of formula I of the invention can be obtained as pharmaceutically acceptable acid addition salts by reacting a free base with an acid, such as hydrochloric, hydrobromic, hydroiodic, nitric, sulfuric, phosphoric, acetic, citric, maleic, succinic, lactic, tartaric, gluconic, benzoic, methanesulfonic, ethanesulfonic, benzenesulfonic, p-toluenesulfonic acid or the like. In a similar manner, the product can be obtained as pharmaceutically acceptable salts by reacting a free carboxylic acid with a base, such as sodium hydroxide, potassium hydroxide, ammonium hydroxide, triethylamine, procaine, dibenzylamine, 1-ephenamine, N,N'-dibenzylethylenediamine, N-ethylpiperidine, arginine, lysine or the like.

The compounds of Formula I of the invention inhibit cholesterol biosynthesis by inhibition of de novo squalene production. These compounds inhibit the squalene synthetase enzyme and, in addition, some of the compounds of Formula I of the invention inhibit other enzymes in the pathway from isopentenyl diphosphate to squalene, that is, farnesyl diphosphate synthetase and isopentenyl diphosphate-dimethylallyl diphosphate isomerase.

Thus, the compounds of the invention are useful in treating atherosclerosis to inhibit progression of disease and in treating hyperlipidemia to inhibit development of atherosclerosis. In addition, the compounds of the invention may increase plasma high density lipoprotein cholesterol levels.

As 1,1-diphosphorus compounds, the compounds of the invention may also be useful in inhibiting formation of gallstones, treating tumors, lowering blood pressure, lowering blood sugar, treating diabetes mellitus, treating inflammation, as a diuretic, as an inotropic agent, as an antiarthritic (antirheumatic) agent, in treating other diseases of calcium and phosphate metabolism including treatment of bone resorption, Paget's disease, osteoporosis, calcification of joints, implants and metastasis, as antitartar and agents in toothpastes and mouthwashes, treating various stones and calculi, treating sickle cell anemia, treating hypoxia and ischemic tissue, and as an anti-ameobal agent, as well as for use in complexes with technetium-99m and radioiodinated derivatives for use as diagnostics.

U.S. application Ser. No. 774,957, filed Oct. 11, 1991, discloses that post-translational modification of CAAX box containing proteins may be inhibited by administering a protein-prenyl transferase inhibitor which inhibits the transfer of the prenyl group [such as farnesyl (in the case of ras oncogene products), geranyl or geranylgeranyl] to the cysteine of the CAAX box by the protein-prenyl transferase enzyme. The protein-prenyl transferase inhibitor will block the protein-prenyl transferase enzyme from catalyzing the transfer of the prenyl group (for example, farnesyl, geranyl or geranyl-geranyl) from the prenyl pyrophosphate to the cys residue of the CAAX box, such as the ras p21 cys, or to the CAAX box cysteine of other CAAX box containing proteins. In the case of ras p21 oncogene products, inasmuch as the cys will not be farnesylated it cannot effect interaction of the ras protein with the membrane so that neoplastic transformation of the cell will be prevented. In this manner protein-prenyl transferase inhibitors prevent neoplastic transformation of the cell, thereby acting as an anti-cancer agent for the treatment of and/or prevention of ras-related tumors.

Aside from ras, examples of CAAX box containing proteins which have been demonstrated or are believed to undergo prenylation include, but are not limited to, nuclear lamins, α or γ subunits of heterotrimeric G-proteins, γ-subunits of retinal transducin, G25K and K-rev p21, and protein families including rho, rap, rac, ral, and rab.

The present invention includes a method for blocking or preventing the prenylation of CAAX box containing proteins such as ras oncogene products, and thereby inhibit disease promoting effects of the CAAX box containing protein or more specifically prevent and/or treat ras-related tumors, by administering to a patient in need of treatment a therapeutic amount of a compound of Formula I of the invention which serves as a protein-prenyl transferase inhibitor.

The Formula I protein-prenyl transferase inhibitors, unlike HMG CoA reductase inhibitors, will interfere with prenylation of the ras oncogene products and inhibit their transforming activity, yet may or may not interfere with the synthesis of FPP, a precursor in the synthesis of ubiquinones, dolichols and Haem A.

The compounds of the invention may also be employed in combination with an antihyperlipoproteinemic agent such as probucol and/or with one or more serum cholesterol lowering agents such as Lopid (gemfibrozil), bile acid sequestrants such as cholestyramine, colestipol, polidexide (DEAE-Sephadex) as well as clofibrate, nicotinic acid and its derivatives, neomycin, p-aminosalicyclic acid, bezafibrate and the like and/or one or more HMG CoA reductase inhibitors such as lovastatin, pravastatin, velostatin or simvastatin.

The above compounds to be employed in combination with the squalene synthetase inhibitor of the invention will be used in amounts as indicated in the Physicians' Desk Reference (PDR).

The compounds of the invention may also be employed with sodium lauryl sulfate of other pharmaceutically acceptable detergents to enhance oral bioavailability of such compounds.

Inhibition of squalene synthetase may be measured by the following procedure.

Rat liver microsomal squalene synthetase activity is measured using farnesyl diphosphate as substrate and quantitating squalene synthesis using gas chromatographic analysis. The assay was developed by modifying conditions originally described by Agnew (Methods in Enzymology 110:357, 1985).

A further aspect of the present invention is a pharmaceutical composition consisting of at least one of the compounds of the invention, such as Formula I, in association with a pharmaceutical vehicle or diluent. The pharmaceutical composition can be formulated employing conventional solid or liquid vehicles or diluents and pharmaceutical additives of a type appropriate to the mode of desired administration. The compounds can be administered to mammalian species including humans, monkeys, dogs, etc., by an oral route, for example, in the form of tablets, capsules, granules or powders, or they can be administered by a parenteral route in the form of injectable preparations. The dose for adults is preferably between 200 and 2,000 mg per day, which can be administered in a single dose or in the form of individual doses from 1-4 times per day.

A typical capsule for oral administration contains active ingredient (250 mg), lactose (75 mg) and magnesium stearate (15 mg). The mixture is passed through a 60 mesh sieve and packed into a No. 1 gelatin capsule.

A typical injectible preparation is produced by asceptically placing 250 mg of sterile active ingredient into a vial, aseptically freeze-drying and sealing. For use, the contents of the vial are mixed with 2 mL of physiological saline, to produce an injectible preparation.

The following Examples represent preferred embodiments of the present invention.

INTRODUCTION TO EXPERIMENTAL

All temperatures are reported in degrees Centigrade.

$^1$H and $^{13}$C chemical shifts are reported as δ-values with respect to Me$_4$Si (δ=0). $^{31}$P spectra were measured on a JEOL FX90Q FT-NMR spectrometer, at 36.2 MHz, or a General Electric QE-300 Plus NMR Spectrometer at 122 MHz, utilizing the $^1$H decoupled mode. The $^{31}$P data were obtained using 85% H$_3$PO$_4$ as an external reference (δ=0). Coupling constants J are reported in Hz. Chemical ionization mass spectra (CI-MS) were determined with a Finnigan TSO-4600 instrument equipped with a direct exposure probe using the indicated reagent gases. Fast atom bombardment mass spectra (FAB-MA) were recorded on a VG Analytical ZAB-2F spectrometer. Ions were sputtered (8keV Xe) from a matrix containing dithiothreitol, dithioerythritol, DMSO, glycerol and water.

All reactions were carried out under an atmosphere of dry argon or nitrogen. The following reagents and solvents were distilled prior to use from the indicated drying agents, where applicable: $CH_2Cl_2$, 2,4,6-collidine, and diisopropylamine ($CaH_2$); THF and diethyl ether (K, benzophenone); N,N-diethyltrimethylsilylamine and oxalyl chloride. Benzene was passed through neutral alumina (activity I) and stored over 4A-molecular sieves. Lithium bromide was dried at 100° C. over $P_2O_5$. (E,E)-Farnesol was purchased from Aldrich Chemical Company.

TLC was performed on E. Merck Silica Gel 60 F-254 plates (0.25 mm) or E. Merck Cellulose F plates (0.1 mm). Flash chromatography was carried out using E. Merck Kieselgel 60 (230-400 mesh)

Reverse-phase chromatographic purification of salts or mixed ester salts was carried on CHP20P gel or SP207SS gel, highly porous, polystyrenedivinyl benzene copolymers available from Mitsubishi Chemical Industries. The indicated general procedure was followed: An FMI Model RP-SY pump was utilized for solvent delivery A column of CHP20P or SP207SS (2.5 cm diameter, 12-22 cm height) as slurry packed and washed with water (500-1000 mL), and a basic, aqueous solution of the crude salt was applied to the top of the column. Typically, the column was eluted with water, followed by a gradient composed of increasing concentrations of acetonitrile or methanol in water. The gradient was created by placing the tip of a tightly stoppered separatory funnel containing 300-500 mL of the organic solvent, or an aqueous-organic mixture, just beneath the surface of a reservoir containing 300-500 mL of pure water. To start the gradient, the stopcock of the separatory funnel was opened, so that as the solvent was withdrawn by the pump from the reservoir, it was replaced with the solvent from the separatory funnel. HPLC-grade solvents were employed. Fractions were collected (10-15 mL each) at a flow rate of 5-10 mL per minute. Those fractions that contained pure product as judged by TLC or HPLC were pooled, the organic solvents were evaporated and the aqueous residue was lyophilized to dryness.

EXAMPLE 1

(E,E)-[1-(hydroxyphosphinyl)-6,10,14-trimethyl-5,9,13-pentadecatrienyl]phosphonic acid, tripotassium salt A. (E,E)-14-Iodo-2,6,10-trimethyl-2,6,10-tetradecatriene A. (1) Bishomofarnesol (a) (E,E)-3,7,11-Trimethyl-2,6,10-dodecatrienyl bromide (farnesyl bromide)

A solution of 1.00 g (4.5 mmol) of (E,E)-farnesol (Aldrich, further purified by flash chromatography) in 10 mL of distilled ether at 0° C. under argon in the dark was treated dropwise with a solution of 195 μL (2.05 mmol, 0.45 eq.) of $PBr_3$ in 2 mL of diethyl ether (ether). The resultant mixture was stirred at 0° C. for one hour, then quenched with water and separated. The organic phase was washed with 5 mL of $H_2O$, 5 mL of saturated $NaHCO_3$, and 5 mL of brine, dried over $Na_2SO_4$ and evaporated to give 1.26 g (98%) of crude bromide as a clear oil.

TLC Silica (2:8 ethyl acetate:hexane) $R_f=0.69$.

$^1$H NMR ($CDCl_3$, 270 MHz): δ 5.52 (t, 1H, J=8.5 Hz), 5.08 (m, 2H), 4.01 (d, 2H, J=8.5 Hz), 2.20-1.90 (m, 8H), 1.73 (s, 3H), 1.68 (s, 3H), 1.60 (s, 6H) ppm.

(b) (E,E)-5,9,13-Trimethyl-4,8,12-tetradecatrienoic acid, 1,1-dimethylethyl ester To a solution of 9.60 mL (68.5 mmol, 1.5 eq.) of diisopropylamine in 100 mL of tetrahydrofuran (THF) at −78° C. under argon was added 28.2 mL (45.0 mmol) of 1.6M n-butyllithium in hexanes over 20 minutes. After warming to 0° C. for 15 minutes, the solution was re-cooled to −78° C. and 6.05 mL (45 mmol) of t-butyl acetate was added over 20 minutes. After an additional 15 minutes, 16.0 mL (92 mmol) of hexamethylphosphoramide (HMPA) was added, followed by a solution of 12.53 g (45.0 mmol) of Part A(1)(a) farnesyl bromide in 100 mL of THF over 20 minutes. The reaction was stirred at −78° C. for 2.5 hours, quenched with saturated $NH_4Cl$ and allowed to warm to room temperature. After diluting with 400 mL of ethyl acetate, the mixture was washed with four 100 mL portions of water, and 200 mL of brine, dried over $MgSO_4$ and evaporated to provide 12.96 g of crude product as a yellow oil. Purification by flash chromatography on 1 kg of silica gel, eluted with 1:9 ethyl acetate:petroleum ether afforded 9.39 g (65%) of title compound as a pale yellow oil.

TLC Silica gel (2:98 ethyl acetate:hexane) $R_f=0.16$.

IR(neat) 2977, 2925, 2857, 1733, 1452, 1368, 1258, 1149 cm$^{-1}$.

$^1$H NMR($CDCl_3$, 270 MHz): δ 5.10 (m, 3H), 2.25 (m, 4H), 2.10-1.90 (m, 8H), 1.68 (s, 3H), 1.62 (s, 3H), 1.59 (s, 6H), 1.44 (s, 9H) ppm.

Mass Spec (CI—$CH_4/N_2O$)

(+ions) m/e 165 (M+H−$C_4H_8$), 247, 183, 137, 68, 57.
(−ions) m/3 319 (M-H), 279, 251, 100.

(c) Bishomofarnesol

To a stirred solution of 5.00 g (15.6 mmol) of Part A(1)(b) compound in 45 mL of dry diethyl ether at 0° C. under argon was added 592 mg (15.6 mmol) of lithium aluminum hydride, and the resulting suspension was stirred at room temperature for 20 hours. After cooling to 0° C., the reaction was quenched by treating with 5 mL of $H_2O$, 5 mL of 15% NaOH, and 15 mL of $H_2O$ and stirring the suspension for ½ hour. After adding $Na_2SO_4$, the slurry was filtered through Celite, washing well with diethyl ether and evaporated to obtain 3.62 g of crude product. Purification by flash chromatography on 300 g of silica gel, eluted with 1:9 ethyl acetate:petroleum ether provided 3.516 g (90%) of bishomofarnesol as a colorless liquid.

TLC Silica gel (2:8 ethyl acetate (EtOAc):hexane) $R_f=0.19$.

IR(neat) 3330, 2964, 2926, 2873, 2958, 1448, 1384, 1107, 1059, 401 cm$^{-1}$.

$^1$H NMR($CDCl_3$, 270 MHz): δ 5.10 (m, 3H), 3.63 (t, 2H, J=6.5 Hz), 2.20-1.90 (m, 10H), 1.68 (s, 3H), 1.62 (s, 3H), 1.60 (s+m, 8H) ppm.

Mass Spec (CI—$CH_4/N_2O$, +ions) m/e 251 (M+H), 249 (M+H−$H_2$). 137, 123, 109, 69.

A.(1) (a) Bishomofarnesol (alternative preparation)

(1)a (E,E)-(3,7,11-Trimethyl-2,6,10-undecadienyl)propanedicarboxylic acid, diethyl ester To a suspension of 1.62 g (40.5 mol, 3 eq.) of a 60% suspension of sodium hydride in mineral oil (washed three times with pentane) in 150 mL of tetrahydrofuran at room temperature under argon was slowly added 6.15 mL (40.5 mmol, 3 eq.) of diethyl malonate. The resulting solution was stirred for 0.5 hours, then treated with a solution of 3.83 g (13.5 mmol) of farnesyl bromide in 10 mL of tetrahydrofuran. After stirring for 6 hours, the reaction was quenched with saturated $NH_4Cl$ and diluted with 300 mL of diethyl ether. The organic layer was washed with two 100 mL portions of water and 100 mL of brine, dried over $MgSO_4$ and evaporated and the bulk of the diethyl malonate removed by spinning under high vacuum to afford 4.29 g (87%) of crude title product.

TLC Silica gel (ethyl acetate:hexane 1:9) $R_f=0.37$. (TLC shows slight amount of diethyl malonate and a second by-product).

(b) (E,E)-5,9,13-Trimethyl-4,8,12-tetradecatrienoic acid, ethyl ester

A mixture of 4.103 g (11.2 mmol) of Part $A^1$ (1)a diester, 200 μL (11.2 mmol) of water, and 950 mg (22.4 mmol) of lithium chloride in 20 mL of dimethyl sulfoxide was heated at reflux (~190° C.) for four hours. After cooling, the reaction mixture was diluted with 180 mL of a 1:1 mixture of diethyl ether: petroleum ether and washed with five 50 mL portions of water and 50 mL of brine, dried over $MgSO_4$ and evaporated to yield 3.623 g of crude product as a yellow-orange oil. Kugelrohr distillation at 180° C. (meter setting) and 0.025 mm allowed the collection of 2.100 g of a pale yellow oil, which was, however, still contaminated (by TLC). The distillation, therefore, is unnecessary and should not be performed. Flash chromatography on 180 g of silica gel, eluted with 3:97 ethyl acetate:petroleum ether provided 1.844 g (56%) of desired title product as a pale yellow oil.

TLC Silica gel (ethyl acetate:hexanes 5:95) $R_f=0.27$ $^1$H-NMR ($CDCl_3$, 270 MHz): δ 5.08 (m, 3H), 4.12 (q, 2H, J=6.7 Hz), 2.31 (m, 4H), 2.10-1.90 (m, 8H), 1.67 (s, 3H), 1.62 (s, 3H), 1.59 (s, 6H), 1.25 (t, 3H, J=6.7 Hz), ppm.

(c) Bishomofarnesol

A solution of 7.05 g (24 mmol) of Part $A^1$(1)(b) monoester in 65 mL of dry diethyl ether at 0° C. under argon was treated in portions with 915 mg (24 mmol) of lithium aluminum hydride and stirred at room temperature for three hours. After cooling to 0° C., the reaction was stirred 0.5 hours, then dried with $Na_2SO_4$. The mixture was filtered through Celite, washing well with diethyl ether, and evaporated to give 5.665 g of a colorless oil. Purification by flash chromatography on silica gel eluted with 15:85 ethyl acetate:petroleum ether provided 5.23 g (87%) of title compound as a colorless oil.

TLC Silica gel (2:8 ethyl acetate:hexanes) $R_f=0.21$.

IR(neat) 3330, 2964, 2926, 2873, 2858, 1448, 1384, 1107, 1059, 401 cm$^{-1}$.

$^1$H NMR ($CDCl_3$, 270 MHz): δ 5.10 (m, 3H), 3.63 (t, 2H, J=6.5 Hz), 2.20-1.90 (m, 10H), 1.68 (s, 3H), 1.62 (s, 3H), 1.60 (s+m, 8H), ppm.

Mass Spec (CI—$CH_4/N_2O$, +ions) m/e 251 (M+H), 249 (M+H—$H_2$), 137, 123, 109, 69.

A(2). (E,E)-5,9,13-Trimethyl-4,8,12-tetradecatrien-1-ol, methanesulfonate ester

To a stirred solution of 2.02 g (8.07 mmol) of bishomofarnesol (prepared as described above) in mL of dichloromethane at 0° C. was added 2.2 mL (16.1 mmol) of triethylamine followed by 0.69 mL (8.90 mmol) of methanesulfonyl chloride, dropwise over 15 minutes. After stirring for 1.5 hours at 0° C., the reaction was diluted with dichloromethane, washed with 20 mL each of 10% HCl, saturated $NaHCO_3$ and brine, dried ($MgSO_4$) and evaporated to give 2.71 g (100%) of the crude title mesylate as a colorless oil.

TLC Silica gel ($CH_2Cl_2$) $R_f=0.46$.

$^1$H NMR ($CDCl_3$, 270 MHz): δ 5.09(t, 3H, J=6.5 Hz), 4.21 (t, 2H, J=7.0 Hz), 2.99 (s, 3H), 2.20-1.90 (m, 10H), 1.78 (quint, 2H, J=7.0 Hz), 1.65 (s, 3H), 1.61 (s, 3H), 1.60 (s, 6H).

A(3)
(E,E)-14-Iodo-2,6,10-trimethyl-2,6,10-tetradecatriene

The crude Part A(2) mesylate prepared from 444.1 mg (1.76 mmol) of the corresponding alcohol according to the procedure of Example 1, Part A(2), was dissolved in 5 mL of acetone and treated with 530 mg (3.52 mmol) of sodium iodide. The reaction was allowed to stir for 16 hours at room temperature followed by 5 hours at reflux. The suspension was diluted with hexane and stirred with dilute aqueous sodium bisulfite to discharge to yellow color. The organic layer was washed with water and brine, dried ($MgSO_4$), and evaporated to provide 577 mg of crude product. Flash chromatography on 35 g of silica gel eluted with hexane gave 550.9 mg (87%) of title iodide as a colorless liquid.

TLC Silica gel (hexane) $R_f=0.31$.

$^1$H NMR ($CDCl_3$, 270 MHz): δ 5.09 (m, 3H), 3.16 (t, 2H, J=7.0 Hz), 2.20-1.90 (m, 10H), 1.85 (quint., 2H, J=6.5 Hz), 1.67 (s, 3H), 1.63 (s, 3H), 1.59 (s, 6H) ppm.

Mass Spec (CI—$CH_4/N_2O$, +ions) m/e 361, 359 (M+H), 137.

B.
(E,E)-(6,10,14-Trimethyl-5,9,13-pentadecatrienyl)phosphonic acid, diethyl ester n-Butyllithium (17.1 mL, 2.5M in hexanes, 42.8 mmol) was added dropwise over 10 minutes to a solution of diethyl methylphosphonate (6.5 mL, 44.6 mmol) in THF (200 mL) at −78° C. under argon. The cloudy white reaction was stirred at −78° C. for 1 hr, whereupon a solution of Part A iodide (13.4 g, 37.2 mmol) in THF (40 mL) was added dropwise over 25 min. The reaction was stirred at −78° C. for 40 minutes, then was allowed to warm to RT over 1 hour. The reaction was quenched by addition of saturated $NH_4Cl$ (30 mL), then diluted with diethyl ether (600 mL). The organic layer was washed with water (100 mL) and brine (2×100 mL), then dried over $MgSO_4$. Evaporation gave a yellow oil which was purified by flash chromatography on silica gel (600 g) eluting with a step gradient of 40:60 EtOAc/hexane to 60:40 EtOAc/hexane to provide title compound (11.8 g, 83%) as a colorless oil.

C. (E,E)-[1-(Ethoxyphosphinyl)-6,10,14-trimethyl-5,9,13-pentadecatrienyl]-phosphonic acid, diethyl ester sec-Butyllithium (26.0 mL, 1.2M in cyclohexane, 31.2 mmol) was added dropwise over 10 minutes to a solution of the Part B compound (10.0 g, 26.0 mmol) in THF (75 mL) at −78° C. The resultant bright yellow reaction was stirred at −78° C. for 1 hour, at which time diethyl chlorophosphite (11.3 mL, 78.1 mmol) was added rapidly all at once. The colorless reaction was stirred at −78° C. for 20 minutes, then allowed to warm to RT over 1 hour. The reaction was stirred at RT for 2.5 hours. Diethyl ether (200 mL) and water (50 mL) were added, and the reaction was stirred vigorously at RT for 30 minutes. The organic layer was washed with water (30 mL) and brine (30 mL), then dried over $MgSO_4$. Evaporation gave a yellow oil which was purified by flash chromatography on CC7 buffered silica gel (500 g) eluting with a step gradient of 3:97 EtOH/EtOAc to 10:90 EtOH/EtOAc to provide title compound (8.20 g, 66%) as a pale yellow oil.

D. (E,E)-[1-Hydroxyphosphinyl)-6,10,14-trimethyl-5,9,13-pentadecatrienyl]phosphonic acid, tripotassium salt Bromotrimethylsilane (677 μL, 5.13 mmol) was added to a mixture of the Part C triester (812 mg, 1.71 mmol) and bis(trimethylsilyl)trifluoroacetamide (682 μL, 2.57 mmol) in $CH_2Cl_2$ (8 mL) under argon. The reaction was stirred at RT overnight. The reaction was then concentrated in vacuo and pumped at high vacuum for 30 minutes. The residue was dissolved in a solution of pyridine in ethanol (3.4 mL, 2.0M, 6.8 mmol) and stirred at RT for 30 minutes. The reaction was concentrated in vacuo and pumped at high vacuum for 30 minutes. The reaction was dissolved in 1N KOH (10.3 mL, 10.3 mmol) and stirred at RT overnight. The aqueous solution was concentrated to a volume of about 3 mL, then chromatographed (2.5×20 cm CHP20P gel) eluting with water, followed by a gradient created by the gradual addition of acetonitrile to a reservoir of water. The product fractions were combined and concentrated to give an opaque gum. Acetone (1 mL) was added and the product was precipitated out as a solid. Filtration and pumping at high vacuum gave 87 mg (10%) of a title product in the form of a beige solid.

MS (ES) m/z 393 (M+4H−3K), 431 (M+3H−2K).

$^1$H NMR (400 MHz, $D_2O$) δ 7.02 (d, 1H, J=525 Hz) 5.16 (t, 1H, J=7 Hz) 5.07 (m, 2H) 1.98 (m, 4H) 1.89 (m, 6H) 1.70–1.30 (m, 4H) 1.54 (s, 3H) 1.50 (s, 3H) 1.47 (s, 6H) ppm.

EXAMPLE 2
[4-[[1,1'-Biphenyl]-4-yl]-1-(hydroxyphosphinyl)butyl]-phosphonic acid, tripotassium salt

A. 4-(3-Iodopropyl)-[1,1'-biphenyl]

A(1) (E)-3-([1,1'-Biphenyl]-4-yl)-2-propenoic acid, methyl ester

Sodium hydride (2.40 g, 60 wt. % in mineral oil, 60.3 mmol) was washed with hexane (2×50 mL), then suspended in THF (125 mL) under argon. Trimethyl phosphonoacetate (9.8 mL, 60.3 mmol) was added to the suspension over 20 min (mild exotherm). A thick precipitate formed and was stirred at RT for 30 min, then at 50° C. for 30 min. After cooling to 0° C., a solution of [1,1'-biphenyl]-4-carboxaldehyde (Aldrich) (10.0 g, 54.9 mmol) in THF (40 mL) was added over 20 min, at which time the precipitate dissolved. The reaction mixture was allowed to stir at 0° C. for 1 h, then at RT for 1 h. The reaction mixture was diluted with $CH_2Cl_2$ and washed with saturated $NH_4Cl$ and water, then dried over $MgSO_4$. Evaporation gave the crude product, which was recrystallized from EtOAc/hexane to afford title ester (7.82 g, 60%) as white plates. The mother liquor was concentrated in vacuo and the resultant solid was recrystallized from MeOH to afford additional title ester (1.90 g, 15% as white plates. Total yield of title ester: 9.72 g (75%).

A(2) [1,1'-Biphenyl]-4-propanoic acid, methyl ester

A mixture of Part A(1) ester (3.0 g, 12.6 mmol) and 10% palladium on carbon (150 mg) in THF (50 mL) was maintained under a balloon of hydrogen for 22 h, then filtered through a layered pad of silica gel under Celite. The solids were washed with THF (200 mL), and the filtrate was evaporated to provide title ester (3.0 g, 99%) as a white solid.

A(3) 4-(3-Iodopropyl)-[1,1'-biphenyl]

Lithium aluminum hydride (17.6 mL, 1.0M in THF, 17.6 mmol) was added dropwise quickly over 15 min. to a solution of Part A(2) ester (4.23 g, 17.6 mmol) in THF (100 mL) at 0° C. under argon. The opaque reaction mixture was stirred at 0° C. for an additional 15 min., then quenched by addition of hydrated $Na_2SO_4$ until gas evolution ceased. The resultant gelatinous suspension was diluted with EtOAc (100 mL), filtered through Celite, and washed with EtOAc (200 mL). The filtrate was evaporated to give 3.80 g of a white solid.

The alcohol prepared above was dissolved in $CH_2Cl_2$ (50 mL) and cooled to 0° C. under argon. Triethylamine (4.9 mL, 35.2 mmol) was added, followed by dropwise addition of methanesulfonyl chloride (1.5 mL, 19.4 mmol) over 5 min. The resultant cloudy yellow reaction mixture was stirred at 0° C. for 15 min., diluted with $CH_2Cl_2$ (200 mL), and washed with 1N HCl (75 mL), saturated $NaHCO_3$ (50 mL), and brine. After drying over $MgSO_4$, the solvent was evaporated to give 5.27 g of a white solid.

The mesylate prepared above was dissolved in acetone (150 mL) under argon. Sodium iodide (13.2 g, 88.0 mmol) was added, and the resultant heterogeneous mixture was heated to and maintained at reflux for 1.5 h, then cooled to RT. The reaction mixture was concentrated in vacuo and the resultant yellow solid was partitioned between $CH_2Cl_2$ (150 mL) and water (75 mL). The organic layer was washed with brine (50 mL), then dried over $MgSO_4$. Evaporation gave a yellow oil, which was purified by flash chromatography on silica gel (75 g) eluting with hexane to give title compound (5.27 g, 93%) as a colorless oil which crystallized on standing.

B. [4-[[1,1'-Biphenyl]-4-yl]butyl]phosphonic acid, diethyl ester n-Butyllithium (20.1 ml, 2.5M solution in hexanes, 50.3 mmol) was added dropwise over 15 minutes to a solution of diethyl methylphosphonate (8.0 ml, 54.5 mmol) in THF (100 ml) at −78° C. under argon. The resultant cloudy white suspension was stirred at −78° C. for 1 hour, at which time a solution of Part A iodide (13.5 g, 41.9 mmol) in THF (30 mL) was added dropwise over 15 minutes. The yellow reaction mixture was stirred at −78° C. for 1 hour, then allowed to warm to RT over 1 hour. The clear orange reaction mixture was generated with saturated NH₄Cl (50 mL). Et₂O (500 mL) was added and the organic layer was washed with H₂O (50 mL) and brine (2×100 ml) then dried over MgSO₄. Evaporation gave a pale yellow oil which was chromatographed on 700 g silica gel eluting with a step gradient of 30:70 EtOAc/hexanes to 40:60 EtOAc/hexanes to 70:30 EtOAc/hexanes to EtOAc to give title compound (7.64 g, 53%) as a yellow oil. Impure product fractions were rechromatographed on 200 g silica eluting with 50:50 EtOAc/hexane to EtOAc to give additional title compound (4.40 g, 30%) as a colorless oil. Total yield: 12.04 g (83%).

C.
[4-[1,1'-Biphenyl]4-yl]-1-(ethoxyphosphinyl)butyl]-phosphonic acid diethyl ester.

sec-Butyllithium (5.93 mL, 1.2M in cyclohexane, 7.12 mmol) was added dropwise over 5 minutes to a solution of Part B diester (2.24 g, 6.47 mmol) in THF (20 mL) at −78° C. The resultant deep orange reaction mixture was stirred at −78° C. for 20 minutes, at which time diethylchlorophosphite (2.82 mL, 19.4 mmol) was added quickly all at once. The reaction immediately went colorless. The reaction mixture was stirred at −78° C. for 1 hour. The cooling bath was removed and the reaction was allowed to warm to RT over 30 minutes, then stirred at RT for 2 hours. Et₂O (50 ml) and H₂O (25 mL) were added and the mixture was stirred at RT vigorously for 1 hour. More Et₂O (100 mL) was added and the organic layer was washed with H₂O (10 ml) and brine (20 ml), then dried over MgSO₄. Evaporation gave a colorless oil which was chromatographed (200 g CC7 buffered silica gel) eluting with a step gradient of EtOAc to 5:95 EtOH/EtOAc to 10:90 EtOH/EtOAc to 15:85 EtOH/EtOAc to give the title compound 1.71 g (60%) as a colorless oil.

D.
[4-[[1,1'-Biphenyl]4-yl]-1-(hydroxyphosphinyl)butyl]-phosphonic acid, tripotassium salt Bromotrimethylsilane (634 μL, 4.81 mmol) was added to a mixture of the Part C triester (677 mg, 1.55 mmol) and bis(trimethylsilyl)trifluoroacetamide (411 μL, 1.55 mmol) in CH₂Cl₂ (7 mL) under argon. The reaction was stirred at RT overnight. Additional bromotrimethylsilane (204 μL, 1.55 mmol) was added, and the reaction was stirred at RT again overnight. The reaction was then concentrated in vacuo and pumped at high vacuum for 1.5 hours. The residue was dissolved in a solution of pyridine in ethanol (1.8 mL, 3.0M, 5.4 mmol) and stirred at RT for 30 minutes. The reaction was concentrated in vacuo and pumped at high vacuum for 30 minutes. The resultant foamy residue was dissolved in 1N KOH (9.3 mL, 9.3 mmol) and stirred at RT for 2 hours. The reaction was diluted with water (5 mL) and lyophilized. The crude product was chromatographed (2.5×20 cm SP207 gel) eluting with water, followed by a gradient created by the gradual addition of acetonitrile to a reservoir of water. The product fractions were combined and lyophilized to give 354 mg (49%) of title compound in the form of a white solid.

MS (FAB, +ions) m/z 431 (M+2H−K), 469 (M+H), 507 (M+K).

IR (KBr): 2938, 2290, 1634, 1562, 1487, 1165, 1074, 957 cm⁻¹.

$^1$H NMR (400 MHz, D₂O) δ 7.56 (d, 2H, J=8.1 Hz) 7.50 (d, 2H, J=8.1 Hz) 7.37 (t, 2H, J=7.5 Hz) 7.31 (d, 2H, J=8.1 Hz) 7.27 (t, 1H, J=7.3 Hz) 7.05 (d, 1H, J=524 Hz) 2.58 (t, 2H, J=7.3 Hz) 1.82-1.55 (m, 6H) ppm.

$^{13}$C NMR (100 MHz, D₂O) δ 143.13 140.59 137.97 129.42 129.20 127.52 126.97 126.87 44.15 35.30 32.40 24.89 ppm.

EXAMPLE 3
(E)-[1-(Hydroxyphosphinyl)-6,10-dimethyl-5,9-undecadienyl]phosphonic acid, trisodium salt A. (E)-5,9-Dimethyl-4,8-decadien-1-ol A.(1) (E)-8-Chloro-2,6-dimethyl-2,6-octadiene To a stirred solution of 30.0 g (0.194 mol) of (E)-3,7-dimethyl-2,6-octadien-1-ol (geraniol) and 28.27 mL (0.213 mol) of 2,4,6-collidine under argon at room temperature was added dropwise 8.23 g (0.194 mol) of lithium chloride in 100 mL of DMF. The mixture was cooled to 0° C. and treated with 16.56 mL (0.213 mmol) of methanesulfonyl chloride dropwise over 10 minutes. The reaction was stirred at 0° C. for 1.5 hours (solid present), then was poured into 500 mL of ice/water. The aqueous solution was washed three times with 200 mL portions of hexane, the organic layers were combined and washed with 5% KHSO₄, water, NaHCO₃, brine, dried (MgSO₄) and evaporated to provide 29.95 g of a pale yellow oil. Rapid flash chromatography was performed on 400 g of silica gel, eluting with 3:9 EtOAc/hexane. Pure product fractions were combined and evaporated to provide 25.20 g (75%) of title compound as a pale yellow oil.

TLC Silica gel (8:1 hexane/EtOAc) R$_f$=0.68.

$^1$H—NMR (CDCl₃, 270 MHz): δ 5.44 (m, 1H), 5.08 (m, 1H), 4.09 (d, 2H, J=8.2 Hz) 2.08 (m, 4H), 1.73 (s, 3H), 1.68 (s, 3H), 1.60 (s, 3H) ppm.

A.(2) (E)-(3,7-Dimethyl-2,6-octadienyl)propanedioic acid, diethyl ester

To a stirred solution of 14.68 g (0.611 mol) of NaH (100%) in 400 mL of THF at 0° C. under argon was added dropwise 92.76 mL (0.611 mol) of diethyl malonate in 100 mL of THF over 0.5 hours. This solution was stirred for 0.5 hours at 0° C., at which time 35.20 g (0.204 mol) of Part (1) chloride in 50 mL of THF was added dropwise over 15 minutes. The reaction gradually warmed to room temperature, stirred for 18 hours then was quenched with 250 mL of saturated NH₄Cl and diluted with 250 mL of ether. The organic layer was washed with water, brine, dried (MgSO₄) and evaporated to remove solvent and provide 100 g of an oil. The excess diethyl malonate was removed by distillation at 75° C. (1.5 mm) to provide 65 g of title compound also containing some dialkylated product and diethyl malonate.

TLC Silica gel (1:1 Hexane/Ethyl acetate) Rf=0.37.

IR (CCl₄) 2982, 2926, 2854, 1751, 1734, 1446, 1369, 1332, 1269, 1236, 1209, 1149, 1111, 1095, 1035, 860 cm⁻¹.

$^1$H NMR (CDCl₃, 270 MHz): δ 5.07 (q, 2H, J=7.1 Hz), 4.18 (q, 2H, J=7.0 Hz), 3.33 (t, 1H, J=7.6 Hz), 2.60 (t, 2H, J=7.3 Hz), 2.04-1.98 (m, 9H), 1.68 (s, 3H), 1.64 (s, 3H), 1.59 (s, 3H), 1.26 (t, 6H, J=7.0 Hz) ppm.

MS (CI—NH₃, +ions) m/e 314 (M+NH₄), 297 (M+H).

A.(3) (E)-5,9-Dimethyl-4,8-decadienoic acid, ethyl ester

To a solution of 65 g of the crude Part (2) diester described above, 5.40 mL (0.30 mol) of water and 25.0 g (0.60 mol) of lithium chloride in 250 mL of DMSO was heated to 190° C. and stirred for 9 hours. The reaction was treated with a 1:1 solution of hexane/ether and then washed with water and brine. The organic layer was dried (MgSO$_4$) and evaporated to provide 34.6 g of title compound in the form of a yellow oil. No further purification was performed; the sample was carried on to the next step.

TLC Silica gel (95:5 Hexane/Ethyl acetate) R$_f$=0.30.

$^1$H NMR (CDCl$_3$, 270 MHZ): δ 5.00 (m, 2H), 4.04 (q, 2H, J=7.0 Hz), 2.23 (m, 4H), 1.99–1.87 (m, 4H), 1.59 (s, 3H), 1.54 (s, 3H), 1.51 (s, 3H), 1.17 (t, 3H, J=7.0 Hz) ppm.

MS (CI—NH$_3$, +ions) m/e 242 (M+NH$_4$), 225 (+H).

A.(4) (E)-5,9-Dimethyl-4,8-decadien-1-ol

To a stirred solution of 5.84 g (0.154 mol) of lithium aluminum hydride in 700 mL of ether at 0° C. under argon was added dropwise 34.50 g of crude Part (3) ester over 20 minutes. The mixture was stirred for 1.5 hours at which time it was quenched by the following: 5.8 mL (0.324 mol) of water, 5.8 mL of 15% NaOH in water and then 17.5 mL (0.973 mol) of water. The granular solution was stirred and dried (MgSO$_4$) for 0.5 hours at which time the mixture was filtered through a celite cake and washed with ether followed by dichloromethane. The filtrate was evaporated to provide 28.16 g of an oil that was distilled using a shortpath apparatus (bp 95°-96° C., 0.3 mm) to provide 20.5 g (55% overall from Part (1) chloride) of title alcohol as a colorless oil.

TLC Silica gel (Dichloromethane) R$_f$=0.11.

IR (CC14) 3620, 3340, 2966, 2924, 2877, 2856, 2729, 1670, 1446, 1377, 1350, 1278, 1199, 1155, 1107, 1057, 985, 829, 814, 792 cm$^{-1}$.

$^1$H NMR (CDCl$_3$, 270 MHz): δ 5.10 (m, 2H), 3.62 (t, 2H, J=6.5 Hz), 2.11–1.94 (m, 7H), 1.67–1.58 (m, 2H), 1.67 (s, 3H), 1.61 (s, 3H) ppm.

MS (CI—NH$_3$, +ions) m/e 200 (M+NH$_4$), 183 (M+H).

B. (E)-10-Iodo-2,6-dimethyl-2,6-decadiene

To a stirred mixture of Part A alcohol (5.00 g, 27.5 mmol), triphenylphosphine (7.57 g, 28.9 mmol), and imidazole (3.93 g, 57.8 mmol) in THF (150 mL) at RT under argon was added a solution of iodine (7.34 g, 28.9 mol) in THF (25 mL) over 20 min. The orange reaction mixture was stirred at RT for 30 minutes, then diluted with hexane (500 ml). The orange suspension was washed with 10% sodium bisulfite, saturated NaHCO$_3$, and brine (100 mL each), then dried over MgSO$_4$. The solids were filtered off and silica gel (30 g) was added to the filtrate. The mixture was evaporated to give a white powder, which was purified by flash chromatography on silica gel (100 g) eluting with hexane to give the title compound (8.11 g, 100%) as a colorless oil.

C. (E)-(6,10-Dimethyl-5,9-undecadienyl)phosphonic acid, diethyl ester

To a stirred solution of diethyl methylphosphonate (4.4 mL, 30.4 mmol) in THF (50 mL) at −78° C. under argon was added n-butyllithium (17.4 mL, 1.6M in hexanes, 27.8 mmol) dropwise over 10 minutes. The resultant cloudy white suspension was stirred at −78° C. for 45 minutes, followed by addition of a solution of Part B compound (7.39 g, 25.3 mmol) in THF (5 mL) dropwise over 15 minutes. The cloudy white reaction mixture was stirred at −78° C. for 3 hours, then allowed to warm to RT over 2 hours. The reaction mixture was quenched by addition of saturated NH$_4$Cl (25 mL) and diluted with Et$_2$O (300 mL). The organic layer was washed with water (20 mL) and brine (50 mL), then dried over MgSO$_4$. Evaporation gave a pale yellow oil, which was purified by flash chromatography on silica gel (500 g) eluting with a gradient of 30:70 to 100:0 EtOAc/hexane to give the title compound (7.25 g, 91%) as a pale yellow oil.

TLC Silica gel (30:70 EtOAc/hexane) R$_f$=0.15.

$^1$H NMR (CDCl$_3$, 270 MHz)

δ 5.11 (m, 2H).
4.09 (m, 4H).
2.00 (m, 6H)
1.80–1.50 (m, 4H)
1.68 (s, 3H)
1.60 (s, 6H)
1.42 (quintet, 1H, J=7.0 Hz)
1.32 (t, 6H, J=7.0 Hz) ppm.

D. (E)-[1-(Hydroxyphosphinyl)-6,10-dimethyl-5,9-undecadienyl]phosphonic acid, triethyl ester To a stirred solution of Part C compound (3.00 g, 9.49 mmol) in THF (35 mL) at −78° C. under argon was added sec-butyllithium (8.8 mL, 1.3M in cyclohexane, 11.4 mmol) dropwise over 10 minutes. The yellow reaction mixture was stirred at −78° C. for 75 minutes, followed by rapid addition of diethyl chlorophosphite (4.1 mL, 28.5 mmol) in one portion. The resultant colorless solution was stirred at −78° C. for 1 hour, allowed to warm to RT over 1.5 hours, and stirred at RT for 2 hours. The reaction mixture was cooled to 0° C., whereupon Et$_2$O (50 mL) and water (20 mL) were added. After stirring at 0° C. for 15 minutes, the ice bath was removed, and the reaction mixture was stirred at RT for 15 minutes. More Et$_2$O (50 mL) was added and the organic layer was washed with water (2×20 mL) and brine (20 mL), then dried over MgSO$_4$. Evaporation gave a crude oil which was purified by flash chromatography on CC7 buffered silica gel (125 g) eluting with a gradient of 3:97 to 5:95 EtOH/CH$_2$Cl$_2$ to give the title compound (2.72 g, 70%) as a pale yellow oil. Title compound is approximately a 2:1 mixture of diastereomers as determined by $^{13}$C NMR.

TLC Silica gel (EtOAc) R$_f$=0.21.

IR (CCL$_4$) 2980, 2932, 2336, 1715, 1551, 1443, 1391, 1236, 1165, 1028, 970, 783 cm$^{-1}$.

$^1$H NMR (CDCl$_3$, 270 MHz)

δ 7.22 (d, 1H, J=572 Hz)
5.03 (m, 2H)
4.10 (m, 6H)
2.18 (m, 1H)
2.10–1.70 (m, 8H)
1.65–1.45 (m, 2H) ·
1.60 (s, 3H)
1.52 (s, 6H)
1.30 (t, 3H, J=7.6 Hz)
1.28 (t, 6H, J=7.3 Hz) ppm.

MS (CI—NH$_3$, +ions) m/e 426 (M+NH$_4$), 409 (M+H).

E. (E)-[1-(Hydroxyphosphinyl)-6,10-dimethyl-5,9-undecadienyl]phosphonic acid, disodium salt To a solution of Part D compound (1.00 g, 2.45 mmol) in CH$_2$Cl$_2$ (10 mL) under argon was added bis(trimethylsilyl)trifluoroacetamide (0.65 mL, 2.45 mmol) followed by bromotrimethylsilane (1.00 mL, 7.60 mmol). The colorless reaction mixture was stirred at RT for 2.75 hours, at which time a solution of pyridine in EtOH (2.9 mL, 3.0M, 8.6 mmol) was added. The resultant mixture was stirred at RT for 1 hour, then concentrated in vacuo. The cloudy white oil was pumped at high vacuum for 45 minutes, then dissolved in 1N NaOH (11.0 mL, 11.0 mmol), and stirred at RT overnight. An additional amount of 1N NaOH (3.7 mL, 3.7 mmol) was added and the reaction mixture was stirred at RT for an additional 3 days, then diluted with water (15 mL) and lyophilized to give an ivory-colored solid. The crude product was purified by column chromatography on SP207 gel (5×20 cm) eluted with water followed by a gradient created by the gradual addition of 70:30 MeOH/H$_2$O (500 mL) to a reservoir of water (500 mL). The product fractions were concentrated to remove acetonitrile, and the aqueous solution was lyophilized to give the title compound (656 mg, 73%) as a white solid.

IR (KBr) 3414, 2967, 2926, 2856, 2315 (P-H), 1450, 1181, 1098, 893 cm$^{-1}$.

$^1$H NMR (D20, 400 MHz) δ 7.00 (d, 1H, J=531 Hz)
5.21 (t, 1H, J=7.0 Hz)
5.15 (t, 1H, J=7.0 Hz)
2.10-1.90 (m, 6H)
1.85-1.40 (m, 5H)
1.63 (s, 3H)
1.58 (s, 3H)
1.57 (s, 3H).

MS (FAB, ions) m/e 391 (M+Na), 369 (M+H), 347 (M+2H-Na), 325 (M.3H-2Na).

Anal. Calcd. for Cl$_3$H$_{24}$Na$_2$O$_5$P$_2$ . 0.75 H$_2$O:
C, 40.90; H, 6.73; P, 16.22,.
Found: C, 40.75; H, 6.70; P, 16.42.

Following the procedure of Examples 1 to 3, the following compounds of the invention may be prepared:

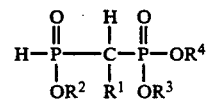

wherein R$^2$, R$^3$ and/or R$^4$ are H, alkyl and/or alkali metal and R$^1$ is as follows:

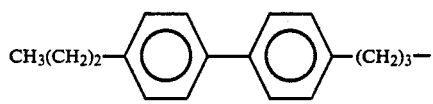

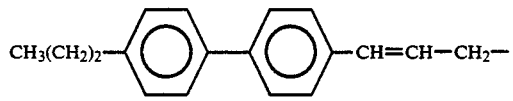

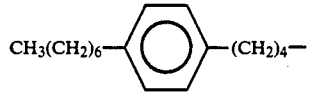

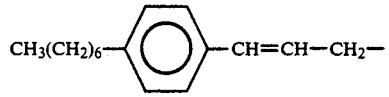

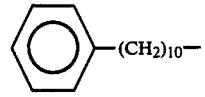

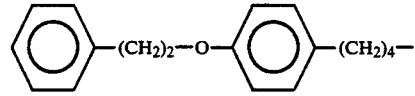

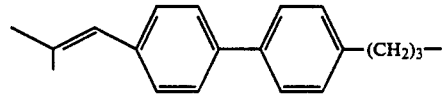

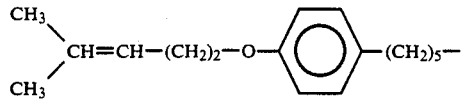

-continued

CH₃(CH₂)₄—O—[naphthalene]—(CH₂)₃—

[biphenyl]—(CH₂)₆—

CH₃(CH₂)₄—O—[naphthalene]—(CH₂)₂— n-C₅H₁₁—[biphenyl]—(CH₂)₃— n-C₅H₁₁—[biphenyl]—CH=CH—CH₂—

[phenyl]—(CH₂)₄—C(CH₃)=CH—(CH₂)₃—

[phenyl]—O—[phenyl]—(CH₂)₃—

[phenyl]—(CH₂)₇— n-C₃H₇—[phenyl]—O—[phenyl]—(CH₂)₃—

C₁₄H₂₉— n-C₃H₇—[phenyl]—O—(CH₂)₆—

(CH₃)₂C=CH—CH₂—CH₂—C(CH₃)=CH—CH₂—CH₂—CH₂—CH₂—

(CH₃)₂C=CH—CH₂—CH₂—CH₂—CH₂—CH₂—CH₂—

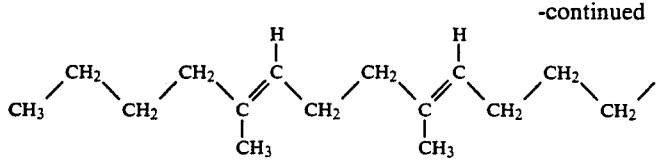

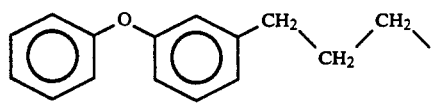

What is claimed is:

1. A compound having the structure

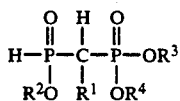

wherein $R^2$, $R^3$ and $R^4$, are independently H, alkyl, aryl, or a metal ion; and $R^1$ is a lipophilic group containing at least 6 carbons, and including pharmaceutically acceptable salts thereof.

2. The compound as defined in claim 1 wherein $R^1$ is alkyl, alkenyl, alkynyl or aryl.

3. The compound as defined in claim 1 wherein $R^1$ is alkenyl containing from 7 to 25 carbon atoms in the chain and from 1 to 4 double bonds; alkynyl containing 1 to 4 triple bonds; mixed alkenyl-alkynyl containing 1 to 3 double bonds and 1 to 3 triple bonds, and where in the above groups alkyl, alkenyl and/or alkynyl may be substituted or unsubstituted; or a group of the structure

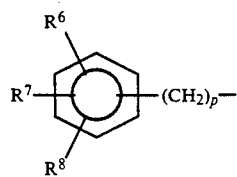

wherein $(CH_2)_p$ contains from 1 to 15 carbons in the chain, that is, p is 1 to 5, and may be modified to include 0, 1, 2 or 3 double bonds and/or 0, 1, 2 or 3 triple bonds in the normal chain, and/or may include 0, 1, 2 or 3 substituents; and $R^6$, $R^7$ and $R^8$ are the same or different and are H, alkyl containing 1 to 40 carbons, alkoxy containing 1 to 40 carbons, alkenyl containing 2 to 40 carbons, alkenyloxy containing 2 to 40 carbons, alkynyl containing 2 to 40 carbons, alkynyloxy containing 2 to 40 carbons, aryl, aryloxy, hydroxy, halogen, nitro, amino, thiol, alkylthio, arylthio, alkylsulfinyl, arylsulfinyl, alkyl-sulfonyl, arylsulfonyl, carboxy, alkoxycarbonyl, aminocarbonyl, alkylcarbonyloxy, arylcarbonyloxy, arylcarbonylamino or alkylcarbonylamino.

4. The compound as defined in claim 1 wherein $R^1$ contains 6 to 20 carbons.

5. The compound as defined in claim 1 wherein $R^1$ is alkenyl.

6. The compound as defined in claim 1 wherein $R^1$ is biphenyl.

7. The compound as defined in claim 1 wherein one or more of $R^2$, $R^3$ and $R^4$ are H.

8. The compound as defined in claim 1 wherein one or more of $R^2$, $R^3$ and $R^4$ are an alkali metal ion or an alkaline earth metal ion.

9. The compound as defined in claim 3 wherein at least one of $R^6$, $R^7$ and $R^8$ is alkenyl, alkenyloxy, alkynyl or alkynyloxy.

10. The compound as defined in claim 1 wherein one or more of $R^2$, $R^3$ and $R^4$ is K or Na.

11. The compound as defined in claim 1 wherein $R^1$ is alkenyl.

12. The compound as defined in claim 1 wherein $R^1$ is

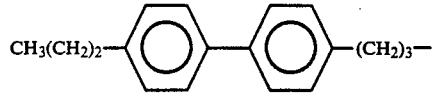

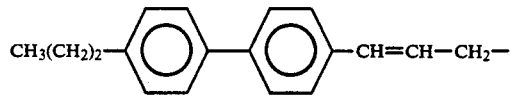

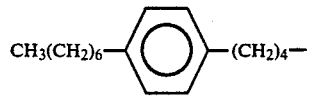

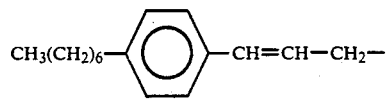

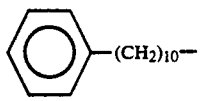
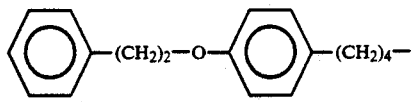
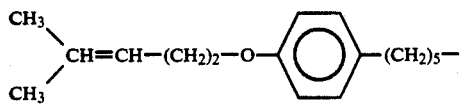
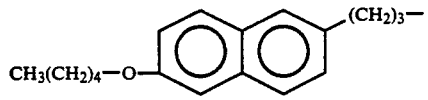
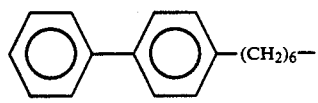
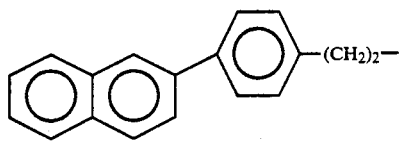
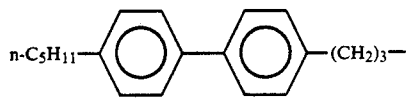
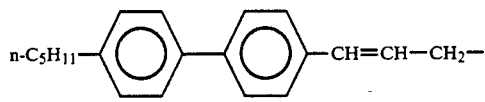
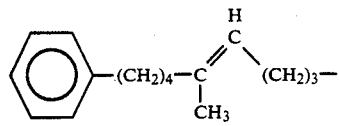
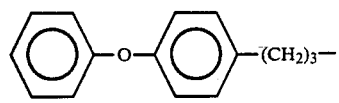
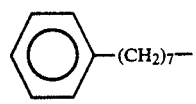
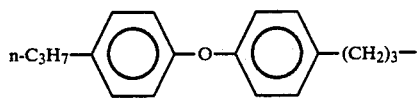
$C_{14}H_{29}-$
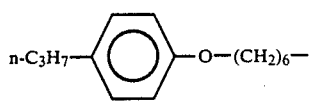

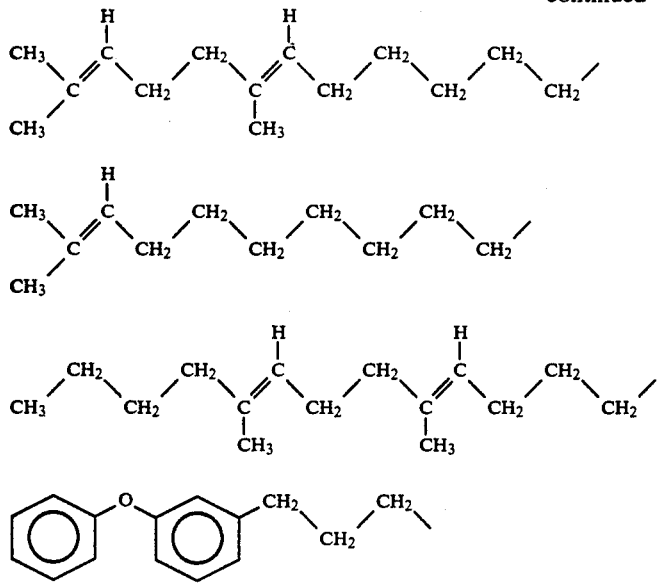

13. The compound as defined in claim 1 which is (E,E)-[1-(ethoxyphosphinyl)-6,10,14-trimethyl-5,9,13-pentadecatrienyl]phosphonic acid, diethyl ester, or its corresponding tripossium or trisodium salt; (E)-[1-(ethoxyphosphinyl)-6,10-dimethyl-5,9-undecadienyl]-phosphonic acid, triethyl ester or its corresponding disodium or dipotassium salt; [4-[[1,1'-biphenyl]-4-yl]-1-(hydroxyphosphinyl)butyl]phosphonic acid, diethyl ester, or its corresponding tripotassium or trisodium salt; (E,E)-[1-(hydroxyphosphinyl)-6,10,14- trimethyl-5,9,13-pentadecatrienyl]phosphonic acid, diethyl ester, or its corresponding tripossium or trisodium salt; (E)-[1-(hydroxyphosphinyl)-6,10-dimethyl-5,9-undecadienyl]-phosphonic acid, diethyl ester or its corresponding trisodium or tripotassium salt; or [4-[[1,1'-biphenyl]-4-yl]-1-(ethoxyphosphinyl)butyl]-phosphonic acid, diethyl ester, or its corresponding tripotassium or trisodium salt.

14. A hypocholestrolemic or hypolipemic composition comprising a compound as defined in claim 1 and a pharmaceutically acceptable carrier therefor.

15. A combination comprising a compound as defined in claim 1 and an antihyperlipoproteinemic agent.

16. The combination as defined in claim 15 wherein said antihyperlipoproteinemic agent is probucol, gemfibrozil, a bile acid sequestrant, clofibrate, nicotinic acid, neomycin, p-aminosalicylic acid, bezafibrate, or an HMG CoA reductase inhibitor.

17. The combination as defined in claim 16 wherein the bile acid sequestrant is cholestyramine, colestipol or polidexide.

18. The combination as defined in claim 16 wherein the HMG CoA reductase inhibitor is lovastatin, pravastatin or simvastatin.

* * * * *